US008758834B2

(12) United States Patent
Hirsch

(10) Patent No.: US 8,758,834 B2
(45) Date of Patent: Jun. 24, 2014

(54) METHOD FOR ENHANCING SPORTS SCORES

(71) Applicant: Alan R. Hirsch, Riverwoods, IL (US)

(72) Inventor: Alan R. Hirsch, Riverwoods, IL (US)

( * ) Notice: Subject to any disclaimer, the term of this patent is extended or adjusted under 35 U.S.C. 154(b) by 0 days.

(21) Appl. No.: 13/860,234

(22) Filed: Apr. 10, 2013

(65) Prior Publication Data

US 2013/0230607 A1 Sep. 5, 2013

Related U.S. Application Data

(60) Continuation-in-part of application No. 13/847,166, filed on Mar. 19, 2013, and a continuation of application No. 12/951,250, filed on Nov. 22, 2010, now Pat. No. 8,399,397, and a division of application No. 11/617,039, filed on Dec. 28, 2006, now Pat. No. 7,838,486.

(60) Provisional application No. 60/754,499, filed on Dec. 28, 2005.

(51) Int. Cl.
*A61K 8/00* (2006.01)
*A61K 8/18* (2006.01)
*A61Q 13/00* (2006.01)
*C11B 9/00* (2006.01)
*C11B 9/02* (2006.01)

(52) U.S. Cl.
USPC ................................. 424/725; 512/1; 512/5

(58) Field of Classification Search
CPC . A61K 36/63; A61K 8/0208; A63B 2209/00; A63B 59/06; B27N 1/00; A61Q 13/00; A61Q 19/10
USPC .......................................... 424/725; 514/1, 5
See application file for complete search history.

(56) References Cited

U.S. PATENT DOCUMENTS

| | | | |
|---|---|---|---|
| 5,380,765 A | 1/1995 | Hirsch | |
| 5,455,043 A | 10/1995 | Fischel-Ghodsian | |
| 5,492,934 A | 2/1996 | Hirsch | |
| 5,759,521 A | 6/1998 | Hirsch | |
| 5,885,614 A | 3/1999 | Hirsch | |
| 5,904,916 A | 5/1999 | Hirsch | |
| 5,949,522 A | 9/1999 | Manne | |
| 6,019,101 A | 2/2000 | Cotner et al. | |
| 6,073,086 A | 6/2000 | Marinelli | |
| 6,089,227 A | 7/2000 | Nilsson | |
| 6,106,837 A | 8/2000 | Hirsch | |
| 6,769,428 B2 | 8/2004 | Cronk et al. | |
| 6,803,987 B2 | 10/2004 | Manne | |
| 6,866,041 B2 | 3/2005 | Hardy, Jr. et al. | |
| 7,067,162 B1 | 6/2006 | Hirsch | |
| 7,108,872 B1 | 9/2006 | Hirsch | |
| 7,160,213 B2 | 1/2007 | Henning | |
| 7,838,486 B2 | 11/2010 | Hirsch | |
| 8,399,397 B2 | 3/2013 | Hirsch | |
| 2002/0189608 A1 | 12/2002 | Raudenbush | |
| 2003/0147938 A1 | 8/2003 | Hirsch | |
| 2004/0137086 A1 | 7/2004 | Hirsch | |
| 2006/0057232 A1 | 3/2006 | Hirsch | |
| 2007/0167348 A1 | 7/2007 | Hirsch | |
| 2008/0086223 A1 | 4/2008 | Pagliarulo | |
| 2012/0165138 A1 | 6/2012 | Smith | |

OTHER PUBLICATIONS

"A Pleasant Scent Can Lead to a Good Night's Sleep," Sense of Smell Institute, http://www.senseofsmell.org/feature/sleep/index.pdf (2009).
Amoore, et al., "Proposal for a Unifying Scale to Express Olfactory Thresholds and Odor Levels: The Decismel Scale," in Proceedings of the 1988 Air Pollution Control Association Annual Meeting, Paper No. 78.5 (21 pp.), Air and Waste Management Association.
Amoore, et al., "Odor as an aid to chemical safety: odor thresholds compared with threshold limit values and volatilities for 214 industrial chemicals in air and water dilution"; Journal of Applied Toxicology, val. 3, No. 6, 1983.
Amoore, et al.. "Practical Test Kits for Quantitatively Evaluating the Sense of Smell." Rhinology, vol. 21, 1983 (pp. 49-54).
Bowlfit test document 2004, Apr. 16, 2004 (retrieved form the internet on Apr. 14, 2009); URL: http://web.archive.org/web/20040416033348/http:I/webpages.charter.nel/bow- Ifil/asian/2000/9. pdf.
Boyce, et al., "The Effects of Self-Efficacy and Goal Setting on Bowling Performance"; Journal of Teaching in Physical Education (JTPE), vol. 16, No. 3, Apr. 1997.
Doty et al., "The Olfactory and Cognitive Deficits of Parkinson's Disease: Evidence for Independence"; American Neurology Association, vol. 25, 1989 (pp. 166-171).
Doty, Richard L., PhD., "The Smell Identification Test: Administration Manual"; 1983: 13-14, Philadelphia: Sensonics, Inc. (1983).
Edwards; Bowling Digest, Aug. 2000, retrieved from internet on Feb. 11, 2009, URL: http://findarticles.com/p/articles/mi.sub.--m0fckis.sub.--3.sub.--18/ai.- sub.--63652458 pp. 1-2).
Gent et al., "Taste and Smell Measurement in a Clinical Setting, in a Clinical Measurement of Taste and Smell"; pp. 107-117, H.L. Meiselman et al. (eds.), 602 pp., MacMillan, N.Y. (1986).
Healthcare International, "Peak Performance Sports Inhaler" (2005)—Main page at http://www.sportsinhaler.com (2 pgs.)—"Product Overview" at http://sportsinhaler.com/productoverview.htm (1 pg.)—"Documented Test Results" at http://www.sportsinhaler.com/d.
Healthcare International, Peak Performance Sports Inhaler, "The Role of Peppermint Odor Administration on Nasal Dilation and Lung Capacity, Brief Report"; 2005 (2 pp.) at http://www.sportsinhaler.com/article.sub.--2hlm.
Healthcare International, News Update & Articles, University Research Leads to World's First 100% All Natural Athletic Enhancer—Peak PerformanceTM Sports InhalerTM, 2005 (2 pp.) at http://www.sportsinhaler.com/newsupdates.htm.
Hirsch et al., Chemical Senses val. 17, No. 5, 1992 (pp. 642, 642-3, 643, 643-4).

(Continued)

*Primary Examiner* — Savitha Rao
(74) *Attorney, Agent, or Firm* — Whyte Hirschboeck Dudek S.C.

(57) ABSTRACT

Methods and compositions for enhancing the score of an individual in a sport activity are disclosed.

10 Claims, No Drawings

(56) References Cited

OTHER PUBLICATIONS

Hirsch. et al., "Validation of the Chicago Smell Test (CST) in Subjective Normosmic Neurologic Patients"; Chemical Senses, vol. 18, No. 5, Oct. 1993.

Ilmberger, et al., "The Influence of Essential Oils on Human Attention, 1: Alertness"; Chemical Senses, vol. 26, No. 3, Apr. 2001 (pp. 239-245).

Koss et al., "Olfactory Detection and Identification Performance and Dissociated in Early Alzheimer's Disease"; Neurology, vol. 38, 1988 (pp. 1228-1232).

MacKenzie, Cheryl, "Peppermint Odor and Athletic Performance: An Ergogenic Aid or an Expectancy Effect?", Powerpoint Presentation, 9 pp., (c. 2005), http://ergo.human.cornell.edu/Grads/CMMDefense%20Presentation%206.15.pdf.

Raudenbush; "Positive Effects of Odorant Administration on Humans—a review"; Sense of Smell, Nov. 18, 2005, pp. 1-29.

Raudenbush, Bryan, "The Effects of Peppermint on Enhancing Mental Performance and Cognitive Functioning, Pain Threshold and Tolerance, Digestion and Digestive Processes, and Athletic Performance"; Wheeling Jesuit University Dept. Psychology, prepared for the Sense of Smell Institute, the Research & Education Division of the Fragrance Foundation (2004) at http://www.senseofsmell.org/papers/B_Raudenbush_peppermint.pdf.

Raudenbush, et al., "Enhancing athletic performance through the administration of peppermint odor"; Brief Report, J. Sport & Exercise Psychology, vol. 23, No. 156, 2001, (4 pp.), at http://www.sportsinhaler.com/article.sub.-1.

Raudenbush, et al., Enhancing Athletic Performance Through the Administration of Peppermint Odor,: Journal of Sport and Exercise Psychology (JSEP), vol. 23, No. 2, Jun. 2001.

Schiffman et al., "Effect of pleasant odors on mood of males at midlife: Comparison of African-American and European-American Men," Brain Research Bulletin, vol. 36, No. 1, 1995 (pp. 31-37).

Strickland, Robert H., "Bowling: Steps to Success (Steps to Success Activity Series)"; Human Kinetics Publishers, Illinois 1996 (p. 1-162).

White, Theresa L., Ph.D., "Aroma-Chology Benefits to Health and Well-Being Scent, Physical Appearance Skin Care"; A Sense of Smell Institute White Paper, Sense of Smell Institute, Apr. 2002.

Yagyu T. abstract. Integrative Psychiatr.. vol. 10, No. 2, 1994 pp. 62-67).

Goldyne, A., et al.; "The Effects of Aroma of Jasmine on Major League Baseball Players"; AChemS XXXIV, 2012 Annual Meeting, Huntington Beach, CA; Apr. 27, 2012; p. 68.

Eighinger, Steve; "Catch a whiff of this: Scent of jasmine could help batters, study suggests"; Herald-Whig; retrieved from the internet on Mar. 29, 2013, http://mobile.whig.com/printerfirendly/FYI-Health-051612; 1 pg.

Chandler, Rick; "Flower Power: Chicago study says whiff of jasmine increases batting performance"; Off the Bench; http://offthebench.nbcsports.com/2012/04/25/flower-power-chicago-study-says-whiff-of-jasmine-increases-batting-performance/; Apr. 25, 2012; 3 pgs.

Vivanco, Leonor; "Smells like a hit: Sox players help test theory jasmine can improve hitting"; RedEye Chicago; http://articles.redeyechicago.com/2012-04-24/sports/31394055_1jasmine-pleasant-odor-smell-taste-treatment; Apr. 24, 2012; 2 pgs.

Constable, Burt; "Study says jasmine could keep Cubs and Sox from stinking—Jasmine improves batting, study finds"; Daily Herald; http://www.dailyherald.com/article-20120415/news/704159904/print/; Apr. 15, 2012; 2 pgs.

"Study: Jasmine helps baseball players"; GantDaily.com; http://gantdaily.com/2012/04/26/study-jasmine-helps-baseball-players/; Apr. 26, 2012; 2 pgs.

"25 Easy Instant Energy Boosters"; Real Simple; retrieved from the internet on Mar. 19, 2013, http://www.realsimple.com/health/mind-mood-emotional-health-easy-instant-energy-boosters-00000000035868-print-index.html; 11 pgs.

"It's all in the wrist: Are 'Jasmine wristbands' the new 'steroid' for baseball pro's?"; HamptonRoads.com; http://hamptonraods.com; Apr. 27, 2012; 1 pg.

Muir, Heather; "Batter Up: Smelling Jasmine Improved Major League Players' Hitting"; Daily Beauty Reporter; http://www.allure.com; Jun. 4, 2012; 2 pgs.

Zezima, Jerry; "A batting tip that makes scents"; StamfordAdvocate; http://www.stamfordadvocate.com/news/article/Zezima-A-batting-tip-that-makes-scents-3686563.php; Jul. 5, 2012; 2 pgs.

Zezima, Jerry; "Batter Up!"; The Huffington Post; http://www.huffingtonpost.com/jerry-zezima/batter-up_b_1658699.html; Jul. 9, 2012; 2 pgs.

METHOD FOR ENHANCING SPORTS SCORES

FIELD OF THE INVENTION

The present invention relates to improving an individual's score or measurement of performance of a sport by the administration of odorants to the individual.

BACKGROUND OF THE INVENTION

The sport of bowling has existed for over 7,000 years, having been discovered in Egyptian ruins in about 5200 BC. Its popularity has persisted over the years and millions of Americans bowl each year. While typically considered to be a recreational sport, bowling has evolved to be part of the current competitive experience. As such, minor variations in bowling score can have substantial impact on outcome. Factors that can influence performance include underlying physical capacity, skill, past learned techniques, hand-eye coordination, degree of alertness, affective state, motivation, self-efficacy, and accuracy in predicting vector analysis concurrent with physical placement of these vectors (Boyce et al., *J. Teaching in Physical Education* 16:312-323 (1997)). In addition, the physical surroundings and ambient environment of a bowler is typically a turbulent sensory invasion: a cacophony of sounds from fellow bowlers and pins falling, a kaleidoscopic image of bowlers blurring the peripheral visual field, and an assault on gestation and olfaction by beer and pizza, superimposed upon by the aroma of stale cigarettes and old bowling shoes. Scientific studies of the effect of these factors on the performance of bowlers is sparse.

Baseball is another popular sport that is played by two opposing teams in which a pitcher throws a baseball toward a batter who attempts to hit the ball with a bat. When a ball is hit, the batter runs a course of four bases to score a run. Therefore, it is important for the batter to be proficient and accurate at hitting the baseball. Batters are not given much time to evaluate a pitch and must react quickly to decide whether or not the ball is hittable and within the strike zone (area through which a pitch must pass relative to the batter to count as a strike if not hit) and also hit the ball with power, skill and accuracy. Many training devices and techniques have been developed to aid in training a batter to accurately swing at a baseball. However, such devices and methods are generally overly complicated, cumbersome or difficult to employ.

Ambient aromas have been demonstrated to impact strength, leisure time activities, and cognitive tests involving precise hand-eye coordination (Raudenbush et al., *J. Sport and Exercise Psychology* 23: 156-160 (2001)). Certain odors have been shown to influence perception on different sensory spheres including perception of age, weight, and external space.

It would be useful to provide a means of enhancing an individual's performance in a sport activity that is non-invasive, convenient, safe, and easy to administer.

DESCRIPTION OF THE INVENTION

The present invention relates to methods of using odorants to enhance an individual's score or other measurement of performance of a sport-related activity by the administration of a composition comprising an odorant or mixture of odorants for sniffing and inhalation by an individual into the nasal passageway. In particular, the method involves delivering an effective amount or concentration of an odorant or mixture of odorants to an individual for continuously inhaling during the performance of a sport to enhance the individual's performance of the sport activity by an improved score or other measurement of performance compared to a base score or base measurement of performance by the individual when the sport activity is performed without inhalation of the odorant.

In an exemplary embodiment of the method, a composition is administered to an individual to inhale while bowling that comprises a jasmine odorant as the primary or dominant odor (aroma) of the composition to increase the bowling score of the individual compared the score achieved by the individual without inhaling the jasmine odorant composition by a statistically significant amount ($p<0.05$).

In another embodiment, the method comprises administering to or having an individual (e.g., baseball player) inhale a composition comprising a jasmine odorant as the primary or dominant odor (aroma) of the composition prior to or during a ball batting event (e.g., baseball batting) to enhance the individual's performance in hitting the ball by a statistically significant amount ($p<0.05$) compared to the individual's performance in hitting a ball (e.g., bat speed, trajectory, distance, mechanics, etc.) without inhaling the jasmine odorant composition, for example, using a statistical measure.

As used herein, the term "odorant" refers to an odor-causing chemical compound or mixture of compounds that, when delivered in a gaseous or aerosol medium, can stimulate olfactory and/or trigeminal chemoreceptors in the nasal cavity and cause a physiological or psychological response. A hedonically positive odorant or odorant mixture is one to which the individual has a pleasant or positive reaction to its scent. A hedonically negative odorant or odorant mixture is one to which the individual has a repulsive or negative reaction to its scent. A hedonically neutral odorant or odorant mixture is one to which the individual has neither a positive nor negative reaction.

In a preferred embodiment, the subject individual is presented with the composition containing a suprathreshold concentration (e.g., about 25-55 decismel units) of the odorant or odorant mixture that is near but not so high as to become an irritant (trigeminal), which the individual inhales while performing the activity. The level or concentration of the odorant or odorant mixture within the composition and/or mode of administering the composition is sufficient to overcome competing or conflicting ambient odors that may act to nullify its effect.

An odorant is presented at a "suprathreshold" level when the decismel level or concentration of the odorant is beyond that needed to be detected by a normosmic individual. At its irritative level, the odorant quantity is so high and intense that the odorant stimulates predominantly the trigeminal nerve (for pain) rather than the olfactory nerve and, hence, is perceived as noxious or painful. The irritation threshold of the patient is the lowest concentration of the substance that causes immediate stinging or burning sensations in the nose, or stinging or lacrimation of the eye. (See, J. F. Gent, in *Clinical Measurement of Taste and Smell*, pages 107-166, H. L. Meiselman et al. (eds.), 602 pp., MacMillan, N.Y. (1986); R. L. Doty et al., *Ann. Neurol.* 25: 166-171 (1989); E. Koss et al., *Neurology* 38: 1228-1232 (1988); and R. Doty, *The Smell Identification Test: Administration Manual* 1983: 13-14, Philadelphia: Sensonics, Inc. (1983)).

If desired, prior to the administration of the odorant, the subject individual can undergo olfactory testing according to a test such as the University of Pennsylvania Smell Identification Test (UPSIT), a 40-question forced-choice, scratch-and-sniff identification test, and the Chicago Smell Test, a 3-item detection and identification test (R. Doty, The Smell Identification Test: Administration Manual 1983: 13-14, Philadelphia: Sensonics, Inc. (1983); A. R. Hirsch et al., Chemical Senses 18(5): 570-571 (1993); A. R. Hirsch et al., Chemical Senses 17(5): 643 (1992)).

The subject individual can also be evaluated for olfactory capacity (e.g. loss of smell) according to an olfactory threshold test as known and used in the art. Such a test provides a precise magnitude of loss of smell and classifies the individual as normosmic, hyposmic or anosmic, which is useful in assessing the effectiveness of a particular odorant and/or the required concentration of the odorant, preferably a suprathreshold and near but below irritant level, to provide the desired effect according to the method of the invention. According to that test, an odorant substance such as butyl alcohol, phenyl ethyl alcohol, or pyridine, is combined in an odorless liquid medium to provide a series of dilutions, or binary steps, of the odorant. For each successive binary step up the dilution scale, the odorant is present, for example, at one half the concentration of the preceding step. The highest concentration of the odorant usually provides the substance at an irritant level. The individual is presented with the series of dilutions in ascending order, and is asked to compare each dilution step to at least one control stimulus, such as odorless propylene glycol.

In the art, a "normosmic" individual is one who can detect the odor of a substance without irritant sensations when the odorant is presented with the range of its average normal threshold. A "hyposmic" or "microsmic" individual has reduced capacity of the olfactory nerve being able to detect an odorant substance by its odor at a concentration, or decismel level, above that of a normosmic individual yet below its irritant concentration level. An "anosmic" individual is one who has essentially no olfactory nerve capacity being unable to detect the odor of the odorant substance, but has trigeminal nerve function, being able to detect an odorant substance by means of irritant, tingling sensations when it is present at an irritant concentration. A patient who is able to detect pyridine vapor by means of irritant, tingling sensations caused by stimulation of the trigeminal nerve, but who cannot distinguish a pyridine odor at a lower concentration without such sensation, is considered to be anosmic having no olfactory nerve sensitivity.

Ranges of the average normal threshold for various odorant substances can be found in the art, for example, Amoore and O'Neill, "Proposal for Unifying Scale to Express Olfactory Thresholds and Odor Levels: The "Decismel Scale"," in Proceedings of the 1988 Air Pollution control Association Annual Meeting, Paper No. 78.5 (21 pp.), Air and Waste Management Association, Pittsburgh, Pa. (1988); Amoore and Haotala, "Odor as an Aid to Chemical Safety: Odor Thresholds Compared with Threshold Limit Values and Volatiles for 214 Industrial Chemicals in Air and Water Dilution," J. Appl. Toxicology 3(6):272-290 (1983).

A suprathreshold amount is a concentration of the odorant/odorant mixture that is greater than the average normal threshold concentration of the odorant or mixture. The normal threshold concentration can be determined by administering a series of the same concentrations of the odorant/odorant mixture to a control group of at least 25 individuals who do not have a chemosensory dysfunction, and calculating the mean threshold concentration detected by the group of 25 individuals. Another alternative is to refer to the known threshold concentration value for the odorant/odorant mixture that has been established previously and published by J. Amoore et al., *J. Appl. Toxicology,* 3:272 (1983).

Odor thresholds can be expressed on the decismel scale. The decismel scale is constructed by setting the mean threshold concentration of a chemosensory agent detected by the control group of 20 year olds at the "0" value. A decismel is calculated by dividing the concentration of the odorant detected by the patient by the normal threshold concentration (using the published value or empirically determining the value) and then taking the logarithm of the quotient. The logarithm of the quotient is then multiplied by 20 to obtain the decismel value. Decismel values can be positive or negative. A positive decismel value indicates the patient is less sensitive to the odorant, i.e. has a higher threshold detection concentration. A negative decismel value indicates that the patient is more sensitive to the compound, i.e. has a lower threshold detection concentration. An increase in the threshold concentration value over the mean threshold concentration value of 2 fold corresponds to 6 decismels (or ds). Determination of decismel units is known in the art, as addressed, for example, in U.S. Pat. Nos. 5,380,765 and 5,492,934 (Hirsch).

In another aspect, the invention provides compositions containing an effective amount of an odorant or mixture of odorants such that, when inhaled by an individual while performing a sport activity, the score and/or performance of the individual is substantially improved. Depending on the nature of the sport, this result can be evidenced by an increased score (e.g., bowling) or by a decreased score (e.g., golf) as compared to the individual's score when the activity is performed while not inhaling the odorant composition (i.e., a control). Such an effect can be objectively assessed and measured by the score of a defined parameter (e.g., a defined number of frames in bowling, etc.) when played with and without administration of the odorant composition.

In an exemplary embodiment, the composition contains an effective amount of a jasmine odorant as the dominant (primary) odor or essence to increase an individual's bowling score (based on a defined number of frames) by about 25-30% when directly and continuously inhaled by the individual while performing the activity, compared to the individual's bowling score without inhaling the jasmine odorant composition.

In embodiments in which the composition is inhaled by a baseball player prior to or while at bat, the effect of inhaling the odorant composition on the batter's performance can be evaluated and objectively assessed based on statistical measures of a defined parameter such as batting average (number of hits divided by number of at bats) and/or by sabermetrics measures, for example, on-base percentage (OBP) ((sum of hits plus walks plus hit by pitches) divided by (sum of at bats plus walks plus hit by pitches plus sacrifice flies)), slugging percentage (batter's total bases divided by the at bats), on-base plus slugging (OPS) (sum of on-base percentage plus slugging percentage), among other measures. In embodiments, performance of a batter can also be subjectively evaluated (e.g., on a 1 to 10 scale) by an evaluator such as a scout, trainer, coach or other professional evaluator who observes and evaluates the ability of the batter to hit a pitch, for example, according to bat speed, trajectory, distance and/or hitting mechanics, e.g., follow through, aim, contact with the ball, timing, force of the impact, stance, reaction speed between release of the ball by the pitcher and impact, accuracy of the swing to connect with the ball, accuracy in recognizing the strike zone and not swinging the bat when the ball is outside the strike zone, etc. In another embodiment, performance such as bat speed, trajectory, impact on the ball, reaction speed, etc., can be physically measured by use of devices known and used in the art. Such measurements and/or evaluations can be made of the batter during a batting event with and without inhalation of the odorant composition, and a comparison can then be made to assess the effect of the inhalation of the odorant composition to improve performance.

In an embodiment, the composition comprises an effective amount of a jasmine odorant as the dominant (primary) odor or essence to improve an individual's performance in hitting a baseball based on a defined statistic such as batting average, on-base percentage (OBP), slugging percentage, on-base plus slugging (OPS), among others, when inhaled by the individual while performing the baseball batting activity, compared to the individual's performance without inhaling the jasmine odorant composition. In another embodiment, improvement in performance can be based on an increase in a subjective rating of performance and/or a physical measurement, for example, bat speed, trajectory, distance and/or hitting mechanics.

The concentration of the odorant or mixture of odorants is preferably at a suprathreshold concentration and preferably near but not an irritant concentration at a decismel level of about 25-55 decismel units, preferably greater than 25 decismel units, preferably at about 30-55 decismel units.

The odorant or odorant mixture is provided as a formulated composition of a single essential odorant or a blend (mixture) of the essential odorants to cause the desired effect, and eliminates odorants that compete with or mask the effective odorant(s). The odorant or odorant blend composition can be administered in combination with an odorless carrier such as mineral oil or water, and odorless additives such as preservatives and the like. The odorant composition can be formulated with a viscosity effective to allow for aerosolization or to provide a thick gel or cream.

A preferred odorant composition is a formulation that essentially comprises a jasmine odorant and eliminates odorants that compete with the jasmine odorant accords or notes to provide a full effect on the individual inhaling the odorant composition. A jasmine odorant, and other odorants for use in the present methods, are commercially available as a liquid, essential oil, extract, or other form from a variety of sources, including, for example, Energy Essentials, AromaTech, Inc. (Somerville, N.J.), Florasynth, Inc. (Teterboro, N.J.), International Flavors and Fragrances, Inc. (IFF; New York, N.Y.), among others.

In one embodiment, the composition can consist essentially of a suprathreshold and non-irritant concentration of one or more odorants such that, when inhaled by an individual, the composition is effective to improve a score or other statistical, subjective or physical measurement of performance of the individual in a sport activity by a statistically significant amount compared to the individual's measurement of performance (e.g., score) upon performing said sport activity without inhalation of the composition. For example, the composition can consist essentially of a jasmine odorant in a carrier such that, when inhaled by an individual, the composition is effective to increase the individual's bowling score of a set number of frames by a statistically significant amount compared to the individual's bowling score for the same number of frames without inhaling the composition. In another embodiment, the composition can consist essentially of a jasmine odorant in a carrier such that when inhaled by batter (e.g., baseball batter), the composition is effective to increase a defined statistical measure, a subjective measure and/or a physical measure of batting performance by a statistically significant amount compared to the same measure of batting performance of the batter under the same or substantially similar circumstances without inhaling the composition.

In another example, the composition can be composed of a mixture of odorants in a carrier, including a suprathreshold and non-irritant concentration of a jasmine odorant in combination with a less than suprathreshold concentration of one or more odorants that complement and do not mask the jasmine odorant, such that, when inhaled by an individual, the composition is effective to improve a score and/or other measurement of performance of the individual in a sport activity by a statistically significant amount.

The odorant composition is preferably formulated as a liquid solution or a spray, but can also be provided in the form of a cream, lotion, or other consistency, and can be contained within a liquid pump device, aerosol or non-aerosol spray device, lidded container, a blister pack, or other suitable vessel such as those known and used in the art. The odorant composition can also be contained in a solid form within a capped vessel. It is preferred that the odorant composition is provided in a portable dispenser that is easily transportable and readily accessible. In embodiments, an absorbent material comprising an effective amount of the odorant composition can be utilized, for example, a wristband, headband, scarf, hat, etc., that can be worn by the individual.

In embodiments of conducting the method of the invention, the odorant composition is administered for direct and continuous inhalation by the subject individual during performance of a sport activity. Such administration can be achieved, for example, by applying an effective amount of the odorant composition in an effective concentration directly to the face of the individual below the nostrils, or to a cloth or paper material such as a mask (e.g., a surgical mask, dust-type mask, earloop face mask, and the like) that is then secured over the nostrils of the subject individual.

In another embodiment, the composition can be administered by means of a flexible laminate material (e.g., patch) sized to fit beneath the nose that incorporates the odorant composition and has a pressure-sensitive adhesive layer (covered by a release layer) that allows the material to adhere to skin and which is positioned under the nostrils of the individual, as described, for example in U.S. Pat. No. 6,769,428 (Cronk).

In yet another embodiment, the odorant composition can be administered through the use of a portable delivery device operable to provide continuous delivery of a vaporous emission of the odorant composition through cannulla (tubes) inserted into the nostrils of the individual as described, for example, in U.S. Pat. No. 6,803,987 (Manne). Other delivery systems can be used for delivery of the odorant composition to the individual.

In other embodiments, an effective concentration of the odorant composition can be applied to an absorbent material (e.g., cotton material, etc.) that can be worn by the individual, for example, a wristband, headband, scarf, hat, etc., and can be sniffed prior to and/or during the sport activity.

Odorants or odorant mixtures can be readily screened and assessed for effectiveness in enhancing performance in a sport or sport related activity according to the invention. For example, a composition containing an odorant or mixture of odorants can be administered to an individual for inhalation to evaluate its effect on modifying a score of a sport activity such as bowling, for example, which can be manifested by an increased bowling score compared to the score achieved when the activity is performed without inhaling the odorant composition. In another embodiment, a composition containing an odorant or odorant mixture can be administered to a baseball batter for inhalation prior to and/or during a batting activity to evaluate its effect on increasing a statistical, subjective and/or physical measurement of hitting performance compared to the same measurement taken when the batting activity is performed without inhaling the odorant composition. Optionally, the individual can be questioned as to a positive or negative reaction to the pleasantness of the scent to assess the hedonics of the odorant composition.

An exemplary method of screening a composition formulated with an odorant or a mixture of odorants for effectively altering an individual's sport score or performance can comprise the steps of:

a) having an individual perform a sport activity (for example, bowling a predetermined number of frames) without inhalation of the target odorant composition and tallying the score ("control score");

b) having the individual re-perform the sport activity from step a) while continuously inhaling a suprathreshold but non-irritant concentration of a composition consisting essentially of the test odorant or odorants, and tallying the score to provide a "test score";

c) comparing the control score to the test score to determine the statistical significance between the two scores; and d) eliminating the odorant or odorant mixture as being ineffective to enhance performance of the individual in the sport activity if not statistically significant ($p<0.05$).

In another embodiment, the method of screening and odorant composition can comprise the steps of:

a) having a batter (e.g., a baseball batter) perform a batting exercise for a set number of pitches without inhalation of the target odorant composition and determining and recording the measurement, e.g., statistical measure, subjective measure and/or physical measure ("control measurement");

b) having the batter re-perform the batting exercise from step a) after or during inhaling a suprathreshold but non-irritant concentration of a composition consisting essentially of the test odorant or odorants, and determining and recording the measurement ("test measurement");

c) comparing the control measurement to the test measurement to determine the statistical significance between the two measurements; and d) eliminating the odorant or odorant mixture as being ineffective to enhance or improve performance of the batter if not statistically significant ($p<0.05$).

The screening test as well as the method of the invention can include other steps such as having the inhaling individual identify the composition as hedonically positive, neutral or negative, and testing olfactory ability and/or olfactory capacity of the individual, among other olfactory tests known and used in the art.

According to the invention, a composition comprising the odorant or odorant mixture is continuously dispensed as a vaporous emission to the nostrils of an individual for inhalation of a concentration effective to enhance the individual's score in a sport activity, with bowling being an exemplary activity using a jasmine-based composition. Such an effect can be assessed and measured objectively by comparing the sport score achieved with and without the administration of the odorant composition. In another embodiment, a composition comprising an odorant or odorant mixture can be administered to an individual for inhalation to evaluate its effect on improving performance of a batter (e.g., baseball batter).

The odorant composition can be packaged as part of an article of manufacture, or kit. In one embodiment, the article of manufacture can comprise a container of an odorant composition or, packaged together, a container of a first odorant and a container of a second odorant (etc.) for combining together to form the odorant composition. The odorant composition comprises an odorant or mixture of odorants in a suprathreshold and but non-irritant concentration, and preferably near a non-irritant concentration, effective to substantially enhance an individual's performance (e.g., sports score, bat speed, mechanics, accuracy or other performance criteria) when administered according to the method of the invention. In a preferred embodiment, the composition consists essentially of a jasmine odorant. For example, the article of manufacture can comprise a container of an odorant composition consisting essentially of a jasmine odorant, or of one or more odorants of which a jasmine odorant is the dominant odor or essence.

The article of manufacture can further comprise a device for use in delivery of the composition to a subject individual during the performance of the sport activity, for example, a mask for placement over the nose of the individual, a device for applying the composition directly to the skin under the nostrils of the individual, an absorbent material such as a wristband to be worn by the individual, among others. In embodiments, the article of manufacture can comprise a wristband, headband, scarf, hat, etc., which is packaged with and/or contains an effective amount of the odorant composition, and can be worn by the individual.

The kit can further include one or more elements for testing the individual, which can be separately packaged, including a device for administering odorant(s) for testing olfactory ability of the individual (e.g., UPSIT), and/or a device for administering a series of odorants for testing olfactory threshold of the individual (e.g., pyridine dilution series).

The article of manufacture can further comprise written or other format of instructions (e.g., C.D., video, cassette tapes, etc.) for use of the odorant composition for enhancing sport performance in a method according to the invention, including, but not limited to increasing an individual's bowling score, improving batting performance, etc. In another embodiment, the article of manufacture can comprise packaging material and an odorant composition according to the invention contained within the packaging material, wherein the packaging material comprises a label that indicates that the odorant composition can be used for enhancing sport performance, for example, a sports score or other statistical, subjective and/or physical measure of performance. The article of manufacture can also include an odorant composition and instructions for testing olfactory threshold according methods known in the art. The parts of the article of manufacturing can be contained or separately packaged within a packaging material, such as a box, bag, pouch, and the like.

The invention will be further described by reference to the following detailed example. This example is not meant to limit the scope of the invention that has been set forth in the foregoing description. Variation within the concepts of the invention is apparent to those skilled in the art. The disclosures of the cited references throughout the application are incorporated by reference herein.

EXAMPLE 1

Methods

Twenty subjects, in a randomized fashion, bowled one frame (10 pins) while wearing a blank surgical mask (control, Aroma #1) and one frame while wearing a mask impregnated with a jasmine aroma (odorant) (Aroma #2). The individuals also rated the hedonics of the mask impregnated with the jasmine odorant. The jasmine odorant was from International Flavors & Fragrances, Inc., Hazlet, N.J.

The subjects were handed a sheet of paper to fill out as follows:

Name:
Age:
Aroma #1
Bowling First Ball: _____(# of pins)
Bowling Second Ball: _____(# of pins)
On Scale of 1-10, with 10 being a "very nice smell", 5 being "neutral", and 0 being "don't like smell at all", rate aroma:

Aroma #2
Bowling First Ball: _____ (# of pins)
Bowling Second Ball: _____ (# of pins)
On Scale of 1-10, with 10 being a "very nice smell", 5 being "neutral", and 0 being "don't like smell at all", rate aroma _____:
Results.

The results are shown in the following table. The "Rating" category presents the individual's rating of the hedonics of the blank (control) mask and the odorant mask on a scale of 1-10, in which a rating of five (5) indicated a neutral hedonic, a rating of greater than five (>5) indicated a positive hedonic, a rating of less than five (<5) indicated a negative hedonic.

|  |  | Aroma #1 | | | Aroma #2 | | |
|---|---|---|---|---|---|---|---|
| Subject Number | Age | 1$^{st}$ Ball (# pins) | 2$^{nd}$ Ball (# pins) | Rating (hedonics) | 1$^{st}$ Ball (# pins) | 2$^{nd}$ Ball (# pins) | Rating (hedonics) |
| 1 | 17 | 3 | 5 | 5 | 8 | 2 | 10 |
| 2 | 15 | 1 | 2 | 6 | 6 | 4 | 3 |
| 3 | 14 | 10 | 0 | 5 | 10 | 0 | 8 |
| 4 | 16 | 3 | 4 | 7 | 0 | 8 | 3 |
| 5 | 16 | 0 | 1 | 5 | 0 | 2 | 2 |
| 6 | 15 | 0 | 5 | 5 | 1 | 9 | 6 |
| 7 | 16 | 7 | 1 | 6 | 1 | 2 | 8 |
| 8 | 16 | 5 | 2 | 5 | 9 | 1 | 6 |
| 9 | 17 | 8 | 0 | 5 | 9 | 1 | 8 |
| 10 | 17 | 4 | 2 | 5 | 6 | 3 | 7 |
| 11 | 16 | 2 | 3 | 7 | 3 | 4 | 8 |
| 12 | 17 | 1 | 4 | 4 | 2 | 6 | 5 |
| 13 | 15 | 0 | 7 | 5 | 3 | 4 | 3 |
| 14 | 17 | 9 | 0 | 5 | 1 | 9 | 4 |
| 15 | 16 | 1 | 6 | 6 | 4 | 3 | 8 |
| 16 | 17 | 6 | 4 | 5 | 5 | 5 | 8 |
| 17 | 17 | 6 | 1 | 5 | 10 | 0 | 2 |
| 18 | 16 | 3 | 2 | 6 | 2 | 5 | 7 |
| 19 | 16 | 4 | 1 | 4 | 5 | 5 | 6 |
| 20 | 16 | 8 | 1 | 3 | 7 | 2 | 6 |
| Totals n = 20 | | 81 | 51 | | 92 | 75 | |
| | | | 132 | | | 167 | |
| Totals n = 18 | | 65 | 47 | | 77 | 70 | |
| | | | 112 | | | 147 | |
| Totals n = 14 | | 62 | 36 | | 72 | 78 | |
| | | | 98 | | | 120 | |

The Table below summarizes the results of the bowling scores. It is noted that test subject #3 had two strikes and a hedonic rating of the jasmine odorant ≥5, and test subject #17 had one strike and a hedonic rating of <5.

| | Mean ± SD | | | |
|---|---|---|---|---|
| | Total No. of Pins: | | Difference Score | |
| Sample | Blank Mask (Control) | Scented Mask | (Scented minus Control) | Paired T-test t-score (p-value) |
| n = 20 (full sample) | 6.60 ± 2.28 | 8.35 ± 2.35 | +1.75 ± 2.49 | +3.14 (p = .0053) |
| n = 19 (eliminate #3) | 6.42 ± 2.19 | 8.26 ± 2.38 | +1.84 ± 2.52 | +3.18 (p = .0051) |
| n = 18 (eliminate #3 & #17) | 6.39 ± 2.25 | 8.17 ± 2.41 | +1.78 ± 2.58 | +2.92 (p = .0095) |
| n = 14 (hedonic rating ≥5) | 7.00 ± 1.88 | 8.57 ± 2.03 | +1.57 ± 2.53 | +2.32 (p = .0372) |
| n = 13 (hedonic rating ≥5, and eliminate #3) | 6.77 ± 1.74 | 8.46 ± 2.07 | +1.69 ± 2.59 | +2.35 (p = .0366) |

Discussion.

With the total group of twenty subjects (n=20), the average score when wearing the blank (control) mask was 6.60 pins per frame, whereas the average score when wearing the jasmine odorant mask was 8.35 pins per frame. The results were statistically significant (p<0.05).

Upon eliminating a ceiling effect (i.e., a score of 10 pins per frame on the best ball for subjects #3 and #17, or n=2), of the eighteen remaining subjects (n=18), the average score when wearing the blank (control) mask was an average of 6.39 pins per frame, and when wearing the jasmine mask was an average of 8.17 pins per frame.

A subdivision of the group to those subjects having less than 10 pins per frame on the best ball and who rated the jasmine odorant/aroma as being neutral or better (n=14), had a total score of 7.0 pins per frame with the blank mask, and 8.6 pins per frame with the mask with the jasmine odorant.

The results also demonstrated that the hedonics of the jasmine odorant did not have a significant effect on the bowling scores of the subject individuals.

Conclusion.

Inhalation of a jasmine odorant had a statistically significant effect on improving bowling scores and performance of the tested individuals.

EXAMPLE 2

A study was conducted to determine the effect of administering the aroma of jasmine on the batting performance of Major League Baseball players.

Methods.

Six (6) Major League Baseball players participated in an Institutional Review Board (IRB) exempted study. All subjects underwent the Quick Smell Identification Test (QSIT), a three (3) question scratch-and-sniff smell identification test (Sensonics, Inc., Haddon Heights, N.J.), administered as per manufacturer's recommendation to screen for any gross olfactory deficits (Doty, R. L, Am J Rhinol, 21, 4: 460-473 (2007).

In a consecutively alternating order, the subjects underwent testing while wearing unodorized cotton wristbands (control) followed by similar wristbands that were pre-impregnated with a jasmine odorant at a suprathreshold but not trigeminally irritating level. The subjects were instructed to wear the wristbands and sniff the band once before batting at a standard pitch, which was provided by the same pitcher selected for pitching consistency. After five (5) pitches, the wristbands were switched and the process was repeated. The subject batters then rated the hedonics of the odorant, and their subjective feeling of their swing and perception of batting ability.

The subject batters, the pitcher and the batting coaches were blinded (not informed) as to which band contained the jasmine odor, the nature of the odor and the objective of the experiment.

The same pitcher and batting coaches rated the batting performance of each of the subject batters. Assessment of the batting performance was based on an integration of the mechanics of the swing including trajectory, ball flight, bat speed, correctness of swing and bat swing in zone.

Results.

While all six subjects claimed normal ability to smell on the QSIT, two subjects scored 0/3, two subjects scored 2/3, and two scored 3/3. All subjects reported positive hedonics toward the jasmine odor. All subjects reported better baseball hitting performance with the jasmine odor, i.e., the subjects hit better and follow-through was better. No effect of order of presentation of the control (no odor) and the jasmine odorant was found.

Conclusion.

Inhalation of the jasmine odorant had a statistically significant effect on improving batting performance of the tested individuals.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents. The disclosures of the cited patents, applications, and other references throughout the application are incorporated by reference herein.

What is claimed is:

1. A method of enhancing performance of a batter in a baseball activity, comprising:
    having the batter inhale an effective amount of a composition comprising a suprathreshold but non-irritant concentration of a jasmine odorant prior to or during batting of a baseball such that the batting performance of the batter is improved by a statistically significant amount compared to the batter's performance in the absence of inhaling the composition.

2. The method of claim 1, wherein the composition comprises a concentration of the jasmine odorant greater than an average normal threshold concentration of the jasmine odorant, the concentration being about 25-55 decismel units.

3. The method of claim 1, wherein the composition consists essentially of the jasmine odorant in a carrier, and optional additives.

4. The method of claim 1, wherein the composition comprises a mixture of odorants in a carrier, said mixture of odorants comprising the jasmine odorant as a dominant odorant in combination with a less than suprathreshold concentration of one or more odorants as a secondary odorant that complement and do not mask the jasmine odorant.

5. The method of claim 1, further comprising assessing the batting performance of the batter to determine effectiveness of administering the composition to enhance the batter's performance.

6. The method of claim 1, further comprising, prior to the batter inhaling the composition,
    having the batter bat the baseball and measuring said batting performance, and
    comparing said measurement to a measurement of the batting performance of the batter with inhaling the composition.

7. The method of claim 1, wherein the batting performance is an action selected from the group consisting of bat speed, bat swing accuracy, bat swing in strike zone, ball trajectory, number of hits and ball distance.

8. The method of claim 1, wherein the batting performance is a hitting mechanic selected from the group consisting of follow through, aim, contact with the ball, timing, force of the impact, stance, reaction speed between release of the ball by the pitcher and impact, accuracy of the swing to connect with the ball, and accuracy in recognizing the strike zone and not swinging the bat when the ball is outside the strike zone.

9. The method of claim 1, wherein the batter wears a wrist or arm band containing the odorant composition, and sniffs the band to inhale the composition.

10. The method of claim 1, wherein the batter wears at least one of a wristband, an armband and a headband containing the odorant composition.

* * * * *